US006612985B2

(12) United States Patent
Eiffert et al.

(10) Patent No.: US 6,612,985 B2
(45) Date of Patent: Sep. 2, 2003

(54) METHOD AND SYSTEM FOR MONITORING AND TREATING A PATIENT

(75) Inventors: Michael E. Eiffert, Pittsford, NY (US); Lisa C. Schwartz, Rochester, NY (US)

(73) Assignee: University of Rochester, Rochester, NY (US)

( * ) Notice: Subject to any disclaimer, the term of this patent is extended or adjusted under 35 U.S.C. 154(b) by 0 days.

(21) Appl. No.: 09/793,191

(22) Filed: Feb. 26, 2001

(65) Prior Publication Data

US 2002/0120187 A1 Aug. 29, 2002

(51) Int. Cl.[7] .................................................. A61B 5/00
(52) U.S. Cl. ............................ 600/300; 128/920; 705/2
(58) Field of Search ................................ 600/300, 301; 128/920–923; 705/2, 3

(56) References Cited

U.S. PATENT DOCUMENTS

| 5,908,383 | A | * | 6/1999 | Brynjestad ................... 128/920 |
| 5,954,640 | A | * | 9/1999 | Szabo ......................... 600/300 |
| 6,014,631 | A | * | 1/2000 | Teagarden et al. ............. 705/2 |
| 6,024,699 | A | | 2/2000 | Surwit et al. |
| 6,039,688 | A | * | 3/2000 | Douglas et al. ............. 600/300 |
| 6,223,164 | B1 | * | 4/2001 | Seare et al. ..................... 705/2 |

OTHER PUBLICATIONS

Patient Infosystems Web site [retrieved from the Internet at http://www/ptisys.com/web/news/1998/pr11–10–98.html on Feb. 16, 2001].

"Guidelines for the Diagnosis and Management of Asthma," *National Institutes of Health*, NIH Publication No. 97–4051, pp. 1–148 (1997).

* cited by examiner

*Primary Examiner*—Eric F. Winakur
*Assistant Examiner*—David J. McCrosky
(74) *Attorney, Agent, or Firm*—Nixon Peabody LLP

(57) ABSTRACT

A method for monitoring and treating a patient with one or more diagnosed conditions includes a few steps. A current assessment of each of the diagnosed conditions is determined in a treatment processing system. The current assessment is based on objective data and subjective data about each of the diagnosed conditions from the patient who is at a remote location and on one or more assessment guidelines for each of the diagnosed conditions. Next, an existing treatment plan for each of the diagnosed conditions is updated using the treatment processing system. The updated treatment plan is based on the existing treatment plan, the current assessment and on one or more treatment guidelines for each of the diagnosed conditions. The updated treatment plan for each of the diagnosed conditions is then transmitted to the patient for application by the patient at the remote location.

9 Claims, 16 Drawing Sheets

PROGRAM FOR INTERNET-BASED MONITORING OF ASTHMATICS

SERVER TIME: WEDNESDAY, FEBRUARY 21, 2001 1:00 PM EST

WELCOME JANE! PLEASE REMEMBER TO LOG OUT WHEN YOU ARE FINISHED WITH YOUR SESSION BY USING THE LOGOUT BUTTON ABOVE.

START TODAY'S SESSION          UPDATE MY PROFILE          LOG OUT

IT HAS BEEN 5 DAYS SINCE YOU LAST SUBMITTED YOUR DATA.

---

BASIC INFORMATION:

FIRST NAME: JANE

LAST NAME: DOE

HEIGHT: 66 INCHES

WEIGHT: 0 POUNDS

SMOKING STATUS: NON-SMOKER

YOUR CONTACT INFORMATION:

ADDRESS 1: UNIVERSITY OF ROCHESTER

ADDRESS 2:

CITY: ROCHESTER

STATE: NY

ZIP: 14627

PHONE: (716) 274-4231

EMAIL: bk001i@mail.rochester.edu

PEAK FLOW HISTORY:

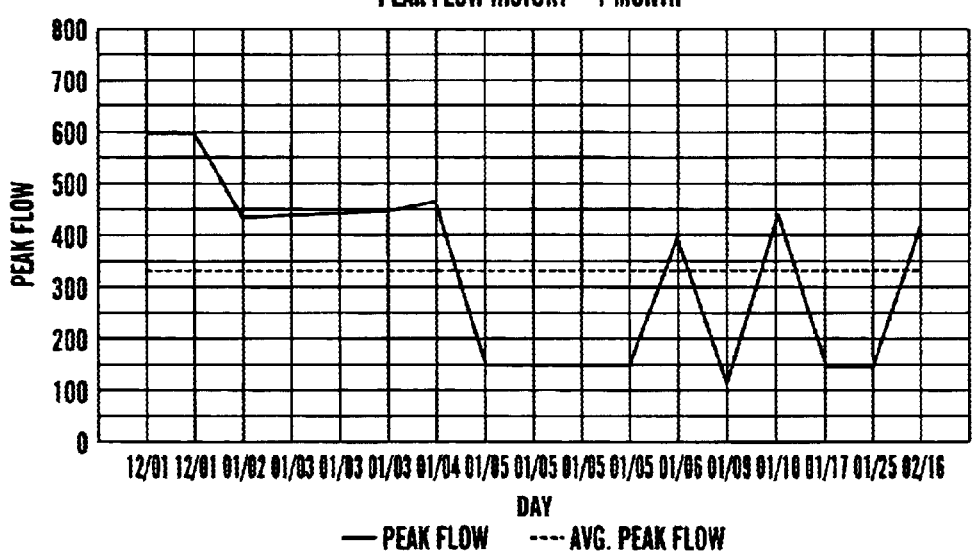

FIG. 7

PROGRAM FOR INTERNET-BASED MONITORING OF ASTHMATICS

SERVER TIME: WEDNESDAY, FEBRUARY 21, 2001 1:00 PM EST

THIS IS THE FIRST PAGE OF YOUR SESSION. PLEASE CHECK YOUR DATA FOR THIS PAGE BEFORE YOU CONTINUE TO PAGE 2.

---

ALBUTEROL INHALER

| | |
|---|---|
| ARE YOU USING AN ALBUTEROL INHALER? | ◉ YES<br>○ NO |
| IF YES, HOW MANY TIMES PER DAY? | [ 2 ▽ ] |
| AND HOW MANY PUFFS EACH TIME? | [ 2 ▽ ] |
| SINCE YOUR LAST SESSION HAVE YOU HAD TO REFILL YOUR PRESCRIPTION FOR ALBUTEROL? | ○ YES<br>◉ NO |

---

SYMPTOMS

| | |
|---|---|
| HOW MANY DAYS SINCE YOUR LAST SESSIONS HAVE YOU HAD SYMPTOMS (COUGHING, WHEEZING, SHORTNESS OF BREATH?) | [ 2 ▽ ] |
| HOW MANY NIGHTS SINCE YOUR LAST SESSIONS HAVE YOU HAD SYMPTOMS (COUGHING, WHEEZING, SHORTNESS OF BREATH?) | [ 2 ▽ ] |
| SINCE YOUR LAST SESSION HAVE YOU HAD MORNING ASTHMA SYMPTOMS NOT RELIEVED BY YOUR ALBUTEROL INHALER? | ○ YES<br>◉ NO |
| SINCE YOUR LAST SESSION HOW MANY TIMES HAVE YOU USED YOUR ALBUTEROL INHALER TO RELIEVE EXERCISE-INDUCED SYMPTOMS? | [ 1 ▽ ] |

---

PEAKFLOW

| | |
|---|---|
| WHAT IS YOUR BEST PEAK FLOW READING SINCE YOUR LAST SESSION? | [ 400 ] |

ONCE YOU HAVE CAREFULLY REVIEWED YOUR DATA FOR THIS PAGE, CONTINUE TO PAGE 2.

*FIG. 8*

PROGRAM FOR INTERNET-BASED MONITORING OF ASTHMATICS

SERVER TIME: WEDNESDAY, FEBRUARY 21, 2001  1:01 PM EST

THIS IS THE SECOND PAGE OF YOUR PIMA DATA SESSION. YOU SHOULD CHECK OVER YOUR DATA ON THIS PAGE BEFORE YOU CONTINUE TO PAGE 3.

---

CORTICOSTEROIDS

ARE YOU USING INHALED CORTICOSTEROIDS?         ● YES
                                                ○ NO

IF YES, WHICH OF THE FOLLOWING INHALED CORTICOSTEROIDS? (SELECT THE LAST OPTION, "OTHER", IF YOUR MEDICATION DOES NOT APPEAR):

[ FLOVENT          ▽ ]

IF YOU CHOSE "OTHER", SPECIFY HERE:

[                  ]

HOW MANY TIMES PER DAY?                         [ 2    ▽ ]

HOW MANY PUFFS WITH EACH USAGE?                 [ 2    ▽ ]

IF YOU ARE TAKING FLOVENT, PLEASE SPECIFY       [ 110 MICROGRAMS ▽ ]
YOUR DOSAGE:

SINCE YOUR LAST SESSION HAVE YOU HAD TO REFILL  ○ YES
YOUR PRESCRIPTION FOR CORTICOSTEROIDS?          ● NO

---

ORAL STEROIDS

ARE YOU USING ORAL STEROIDS SUCH AS PREDNISONE?  ○ YES
                                                 ● NO

---

OTHER ASTHMA/ALLERGY MEDICATIONS

ARE YOU USING OTHER MEDICATIONS FOR ASTHMA      ● YES
OR ALLERGIES?                                    ○ NO

IF YES, CHOOSE YOUR MEDICATION BELOW (SELECT THE LAST OPTION, "OTHER", IF YOUR MEDICATION DOES NOT APPEAR):

[ ZYRTEC           ▽ ]

*FIG. 9A*

PROGRAM FOR INTERNET-BASED MONITORING OF ASTHMATICS

IF YOU CHOSE "OTHER", SPECIFY HERE:

[          ]

SINCE YOUR LAST SESSION HAVE YOU HAD TO REFILL
YOUR PRESCRIPTION FOR OTHER ASTHMA/ALLERGY
MEDICATIONS?
○ YES
⦿ NO

---

SIDE EFFECTS

IF YOU HAVE EXPERIENCED ANY SIDE EFFECTS FROM YOUR ASTHMA-RELATED
MEDICATION, CHOOSE THEM FROM THE LIST BELOW:

☐ HEADACHES
☑ LIGHTHEADEDNESS
☐ RESTLESSNESS
☑ PALPITATIONS
☐ SEDATION
☐ THRUSH
☐ ANXIETY
☐ TREMOR
☐ OTHER

---

RESPIRATORY INFECTION

DO YOU CURRENTLY HAVE A RESPIRATORY INFECTION
(COLD, FLU, BRONCHITIS, SINUSITIS OR PNEUMONIA?)
○ YES
⦿ NO

ONCE YOU HAVE CAREFULLY REVIEWED YOUR DATA FOR THIS PAGE, CONTINUE TO PAGE 3.

*FIG. 9B*

PROGRAM FOR INTERNET-BASED MONITORING OF ASTHMATICS

SERVER TIME: WEDNESDAY, FEBRUARY 21, 2001  1:02 PM EST

THIS IS THE THIRD AND FINAL PAGE OF YOUR PIMA DATA SESSION. ONCE YOU HAVE CHECKED OVER AND SUBMITTED YOUR DATA FOR THIS PAGE, YOU WILL BE ASKED TO REVIEW ALL OF THE DATA FOR THIS SESSION.

---

ATHLETICS

ARE YOU CURRENTLY INVOLVED IN ATHLETICS?  ● YES  ○ NO

IF YES, THEN HOW MANY DAYS SINCE YOUR LAST SESSION HAS YOUR PHYSICAL ACTIVITY BEEN CURTAILED DUE TO YOUR ASTHMA?  [ 0 ▽ ]

HOW MANY DAYS SINCE YOUR LAST SESSION HAVE YOU HAD TO FOREGO ATHLETICS DUE TO YOUR ASTHMA?  [ 0 ▽ ]

---

SATISFACTION AND WELL-BEING

HOW SATISFIED DO YOU FEEL WITH THE CARE YOU ARE RECEIVING?  [ SATISFIED ▽ ]

THINKING OF THE DAYS SINCE YOUR LAST SESSION (INCLUDING TODAY), HOW WOULD YOU RATE HOW HEALTHY YOU HAVE BEEN?  [ FAIR ▽ ]

---

SMOKING

HOW MANY CIGARETTES HAVE YOU SMOKED SINCE YOUR LAST SESSION?  [ NONE ▽ ]

---

CLINICAL/EMERGENCY ROOM/HOSPITAL VISITS AND MISSED WORK OR SCHOOL

SINCE YOUR LAST SESSION HAVE YOU HAD ANY CLINIC VISITS?  ○ YES  ● NO

IF YES, HOW MANY? (ENTER NUMBER)  [          ]

SINCE YOUR LAST SESSION, HAVE YOU HAD ANY VISITS TO THE EMERGENCY ROOM?  ○ YES  ○ NO

IF YES, HOW MANY? (ENTER NUMBER)  [          ]

*FIG. 10A*

PROGRAM FOR INTERNET-BASED MONITORING OF ASTHMATICS

PAGE 2 OF 2

SINCE YOUR LAST SESSION, HAVE YOU BEEN HOSPITALIZED?  ○ YES  ● NO

IF YES, HOW MANY TIMES? ▢

SINCE YOUR LAST SESSION, HAVE YOU MISSED WORK OR SCHOOL DUE TO ASTHMA?  ○ YES  ● NO

IF YES, HOW MANY DAYS? ▢

ONCE YOU HAVE CAREFULLY REVIEWED YOUR DATA FOR THIS SESSION, CLICK ON "REVIEW AND SUBMIT DATA". YOU WILL THEN VIEW ALL YOUR ANSWERS FOR THIS SESSION.

⇨ REVIEW AND SUBMIT DATA

*FIG. 10B*

PROGRAM FOR INTERNET-BASED MONITORING OF ASTHMATICS

SERVER TIME: TUESDAY, FEBRUARY 20, 2001 7:21 PM EST

YOUR DATA HAS BEEN SUCCESSFULLY UPDATED!

YOU SHOULD LOG ON FOR YOUR NEXT SESSION BY WEDNESDAY, JANUARY 21. PLEASE TAKE A NOTE OF THIS DATE. UNTIL THEN, AND AS ALWAYS, THANK YOU!

TO KEEP YOUR DATA SAFE, PLEASE REMEMBER TO FINISH BY LOGGING OUT! YOU CAN DO THIS FROM THIS PAGE OR AFTER RETURNING TO YOUR HOME PAGE TO VIEW YOUR UPDATED PERFORMANCE GRAPH.

 RETURN TO MY HOMEPAGE           LOGOUT

*FIG. 11*

PROGRAM FOR INTERNET-BASED MONITORING OF ASTHMATICS

TUES. FEB. 20 19:20:42 GMT-0500 2001

YOU ARE ALMOST FINISHED WITH THIS SESSION. BE SURE TO REVIEW THE DATA ON THIS PAGE TO MAKE SURE ALL THE DATA IS CORRECT. IF YOU FIND ERRORS, YOU SHOULD REDO THIS SESSION. WHEN YOU ARE FINISHED, PLEASE REMEMBER TO LOG OUT FROM YOUR SESSION.

HERE IS ALL OF THE DATA YOU ENTERED FOR THIS SESSION:

ALBUTEROL INHALER

| | |
|---|---|
| USING AN ALBUTEROL INHALER: | YES |
| NUMBER OF TIMES PER DAY: | 3 |
| NUMBER OF PUFFS EACH TIME: | 2 |
| PRESCRIPTION REFILL FOR ALBUTEROL SINCE YOUR LAST SESSION: | YES |

SYMPTOMS

| | |
|---|---|
| NUMBER OF DAYS SINCE YOUR LAST SESSION HAVE YOU HAD SYMPTOMS (COUGHING, WHEEZING, SHORTNESS OF BREATH): | 4 |
| NUMBER OF NIGHTS SINCE YOU LAST SESSION YOU HAVE HAD SYMPTOMS: | 2 |
| ASTHMA SYMPTOMS NOT RELIEVED BY YOUR ALBUTEROL INHALER SINCE YOUR LAST SESSION: | NO |
| NUMBER OF TIMES SINCE YOUR LAST SESSION YOU USED YOUR ALBUTEROL INHALER TO RELIEVE EXERCISE-INDUCED SYMPTOMS: | -1 |

PEAKFLOW

| | |
|---|---|
| YOUR BEST PAK FLOW READING SINCE YOUR LAST SESSION: | 700 |

*FIG. 12A*

| | |
|---|---|
| CORTICOSTEROIDS | |
| USING INHALED CORTICOSTEROIDS: | YES |
| NAME OF CORTICOSTEROIDS: | AEROBID, AEROBID-M |
| NUMBER OF TIMES CORTICOSTEROIDS USED PER DAY: | 1 |
| NUMBER OF PUFFS WITH EACH USAGE: | 1 |
| CORTICOSTEROID PRESCRIPTION REFILLED SINCE YOUR LAST SESSION: | NO |
| ORAL STEROIDS | |
| USING ORAL STEROIDS SUCH AS PREDNISONE: | YES |
| OTHER ASTHMA/ALLERGY MEDICATIONS | |
| USING OTHER MEDICATIONS FOR ASTHMA OR ALLERGIES: | YES |
| WHICH MEDICATION: | ACCOLATE |
| PRESCRIPTION REFILL FOR OTHER ASTHMA/ALLERGY MEDICATIONS SINCE YOUR LAST SESSION: | NO |
| SIDE EFFECTS | |
| SIDE EFFECTS YOU ARE EXPERIENCING FROM ASTHMA-RELATED MEDICATION: | LIGHTHEADEDNESS SEDATION |
| RESPIRATORY INFECTION | |
| CURRENT RESPIRATORY INFECTION (COLD, BRONCHITIS, SINUSITIS, OR PNEUMONIA) | NO |
| ATHLETICS | |
| CURRENT ATHLETIC INVOLVEMENT: | YES |
| NUMBER OF DAYS SINCE YOUR LAST SESSION THAT PHYSICAL ACTIVITY HAS BEEN CURTAILED BY ASTHMA (IF YES ABOVE): | 1 |
| NUMBER OF DAYS SINCE YOUR LAST SESSION YOU HAVE HAD TO FOREGO ATHLETIC ACTIVITY DUE TO ASTHMA: | -1 |

*FIG. 12B*

SATISFACTION AND WELL-BEING

| | |
|---|---|
| YOUR SATISFACTION WITH THE CARE YOU ARE RECEIVING: | SATISFIED |
| YOUR SUBJECTIVE RATING OF WELL-BEING FOR DAYS SINCE LAST SESSION, INCLUDING TODAY: | GOOD |
| PLAN OF ACTION FOR YOUR ASTHMA SHOULD YOUR SYMPTOMS WORSEN: | YES |

SMOKING

| | |
|---|---|
| APPROXIMATE NUMBER OF CIGARETTES SMOKED SINCE LAST SESSION | 20-30 |

CLINIC/EMERGENCY ROOM/HOSPITAL VISITS AND MISSED WORK OR SCHOOL

| | |
|---|---|
| CLINIC VISITS SINCE LAST SESSION: | YES |
| HOW MANY: | 1 |
| EMERGENCY ROOM VISITS SINCE LAST SESSION: | YES |
| NUMBER (IF YES): | 1 |
| HOSPITAL STAYS SINCE LAST SESSION: | YES |
| NUMBER (IF YES): | 1 |
| HAVE YOU MISSED ANY WORK OR SCHOOL SINCE YOUR LAST SESSION: | YES |
| NUMBER OF DAYS OF WORK/SCHOOL MISSED SINCE YOUR LAST SESSION: | 1 |

ONCE YOUR HAVE CAREFULLY LOOKED OVER YOUR DATA FOR THIS SESSION, CLICK ON FINISH

 FINISH

*FIG. 12C*

METHOD AND SYSTEM FOR MONITORING AND TREATING A PATIENT

FIELD OF THE INVENTION

This invention relates generally to a health care method and system and, more particularly, to a method and system for monitoring and treating a patient who has one or more diagnosed conditions and is located at a remote location from a treatment processing system.

BACKGROUND OF THE INVENTION

Monitoring patients with chronic illnesses, such as congestive heart failure, diabetes and asthma, represents one of the greatest challenges facing medicine today. Patients with chronic illnesses require ongoing, follow up treatment and care to properly manage their conditions. Unfortunately, a number of these patients do not receive ongoing treatment and care, receive ongoing treatment and care on a sporadic basis, or receive ongoing treatment and care which is not in accordance with recommended guidelines. As a result, these patients often unnecessarily suffer from symptoms of their chronic illness which could have been minimized or prevented with proper ongoing treatment and care. Additionally, some of these patients require hospitalization visits which may have been preventable and, tragically, a few of these patients may die as a result of receiving improper ongoing, treatment and care.

More specifically, and by way of example, asthma affects about fifteen million people in the United States. Long term control of asthma is possible with medications such as inhaled steroids, but in order to reduce adverse effects, use of the lowest possible dose is recommended. Determining the proper dosage requires ongoing monitoring of the patient. Monitoring of patient status is possible with the use of simple Peak Flow Meter measurements of breath rate, which the patient can do himself. Unfortunately, many patients with asthma are not properly monitored and cared for on an ongoing basis. Studies of children and adults have found that less than 50% of the patients were receiving anti-inflammatory therapy as recommended by the NIH Guidelines and only 28% of the adult patients had written action plans that told them how to manage their asthma and control an exacerbation, as set forth in the "Practical Guide for the Diagnosis and Management of Asthma," NIH publication 974053, 1997, p. 1. As a result, asthma is the third leading cause of preventable hospitalizations in the United States. Asthma causes 1.5 million emergency room visits, 470,000 hospitalizations and more than 5000 deaths annually, at least a portion of which are preventable.

One possible solution to this problem is internet-based monitoring of patients. Internet-based monitoring of chronically ill patients is in its infancy, but provides an attractive platform for the surveillance of such patients. A trial in 1998 found that patients using Patient Infosystem's internet-based asthma disease management system had: 36% lower health costs; 52% fewer urgent physician visits; and 67% fewer emergency room visits compared to usual care patients as set forth at http://www.ptisys.com/web/news/1998/pr11-10-98.html. These are promising results.

Another approach is disclosed in U.S. Pat. No. 6,024,699 for, "Systems, Methods, and Computer Program Products for Monitoring, Diagnosing, and Treating Medical Conditions of Remotely Located Patients" which is herein incorporated by reference. With this system, method, and product, medical conditions of a plurality of remotely located patients are monitored, diagnosed, prioritized and treated using a central data processing system configured to communicate with and receive data from a plurality of respective patient monitoring systems. Unfortunately, there are a number of limitations with this approach. For example, this approach fails to take into account subjective data on each patient's condition, does not customize a diagnosis and a treatment plan based on the each patient's particular medical history, does not directly notify an emergency service provider in the event of a detected emergency, and does not monitor physician compliance with prescribed treatment guidelines in treating these patients.

SUMMARY OF THE INVENTION

A method for monitoring and treating a patient with one or more diagnosed conditions in accordance with one embodiment of the present invention includes a few steps. A current assessment of each of the diagnosed conditions is determined in a treatment processing system. The current assessment is based on objective data and subjective data about each of the diagnosed conditions from the patient who is at a remote location and on one or more assessment guidelines for each of the diagnosed conditions. Next, an existing treatment plan for each of the diagnosed conditions is updated using the treatment processing system. The updated treatment plan is based on the existing treatment plan, the current assessment and on one or more treatment guidelines for each of the diagnosed conditions. The updated treatment plan for each of the diagnosed conditions is then transmitted to the patient for application by the patient at the remote location.

A system for monitoring and treating a patient with one or more diagnosed conditions in accordance with another embodiment of the present invention includes an assessment processing system and a treatment processing system. The assessment processing system determines a current assessment of each of the diagnosed conditions based on objective data and subjective data about each of the diagnosed conditions from the patient and on one or more assessment guidelines for each of the diagnosed conditions. The treatment processing system updates an existing treatment plan for each of the diagnosed conditions based on the existing treatment plan, the current assessment and on one or more treatment guidelines for each of the diagnosed conditions to generate an updated treatment plan for each of the diagnosed conditions.

A method for monitoring and treating a patient with one or more diagnosed conditions in accordance with another embodiment of the present invention also includes a few steps. First, a current assessment of each of the diagnosed conditions is determined using a treatment processing system. The current assessment is based on data about each of the diagnosed conditions from the patient who is at a remote location and on one or more assessment guidelines for each of the diagnosed conditions. Next, an existing treatment plan for each of the diagnosed conditions is updated using the treatment processing system. The updated treatment plan for each of the diagnosed conditions is generated based on the existing treatment plan, the current assessment, and on one or more treatment guidelines for each of the diagnosed conditions. In this process, at least one of the current assessment or the updated treatment plan for each of the diagnosed conditions is also determined or updated based on one or more customized guidelines.

A system for monitoring and treating a patient with one or more diagnosed conditions in accordance with another embodiment of the present invention includes an assessment processing system and a treatment processing system. The assessment processing system determines a current assessment of each of the diagnosed conditions. The current assessment is based on data about each of the diagnosed conditions from the patient who is at a remote location and on one or more assessment guidelines for each of the diagnosed conditions. The treatment processing system updates an existing treatment plan for each of the diagnosed conditions. The updated treatment plan is generated based on the current assessment and the on one or more treatment guidelines for each of the diagnosed conditions. With this system, at least one of the current assessment or the updated treatment plan for each of the diagnosed conditions is also determined or updated based on one or more customized guidelines for the patient.

A method for monitoring for a patient with one or more diagnosed conditions in accordance with yet another embodiment of the present invention includes a few steps. First, a current assessment of each of the diagnosed conditions is determined using a treatment processing system. The current assessment is based on data about each of the diagnosed conditions from the patient who is at a remote location and on one or more assessment guidelines for each of the diagnosed conditions. Next, a determination is made on whether or not the current assessment indicates an emergency. If the current assessment indicates the emergency, then at least a portion of the data is confirmed with the patient. An emergency service provider is notified of the emergency with the patient if the confirmation of the data from the patient is received.

A system for monitoring for a patient with one or more diagnosed conditions in accordance with yet another embodiment of the present invention includes an assessment processing system, a warning system, a confirmation system, and a notification system. The assessment system determines a current assessment of each of the diagnosed conditions based on data about each of the diagnosed conditions from the patient who is at a remote location and on one or more assessment guidelines for each of the diagnosed conditions. The warning system determines if the current assessment indicates an emergency. The confirmation system confirms at least a portion of the data with the patient if the current assessment indicates the emergency. The notification system that notifies an emergency service provider of the emergency with the patient if the confirmation of the data from the patient is received.

A method for tracking compliance of treatment of patients in accordance with yet another embodiment of the present invention includes a few steps. First, a current assessment of each of the diagnosed conditions is determined using a treatment processing system based on data about each of the diagnosed conditions from the patient who is at a remote location and on one or more assessment guidelines for each of the diagnosed conditions. Next, an existing treatment plan for each of the diagnosed conditions is updated using the treatment processing system based on the existing treatment plan, the current assessment, and on one or more treatment guidelines for each of the diagnosed conditions to generate an updated treatment plan for each of the diagnosed conditions. Next, the patient is provided with a reviewed treatment plan based on the updated treatment plan for each of the diagnosed conditions. Next, compliance data based on the reviewed treatment plans and the updated treatment plans is generated and provided.

A system for tracking compliance in monitoring and treating patients in accordance with yet another embodiment of the present invention includes an assessment processing system, a treatment processing system, a presentation system, and a compliance processing system. The assessment processing system determines a current assessment of each of the diagnosed conditions using a treatment processing system based on data about each of the diagnosed conditions from the patient who is at a remote location and on one or more assessment guidelines for each of the diagnosed conditions. The treatment processing system updates an existing treatment plan for each of the diagnosed conditions using the treatment processing system based on the existing treatment plan, the current assessment, and on one or more treatment guidelines for each of the diagnosed conditions to generate an updated treatment plan for each of the diagnosed conditions. The presentation system provides the patient with a reviewed treatment plan based on the updated treatment plan for each of the diagnosed conditions. The compliance processing system generates and provides compliance data based on the reviewed treatment plans and the updated treatment plans.

The present invention provides a unique method and system for monitoring and treating chronically ill patients with a number of advantages. The method and system are applicable to a myriad illnesses and utilizes the Internet to monitor and treat chronically ill patients. With the present invention not only are costs associated with direct treatment by the physician reduced, but also patient compliance to his/her treatment protocol and compliance by the physician to standard NIH treatment guidelines or guidelines from other authoritative organizations is also reinforced.

The present invention develops ongoing treatment plans that more effectively respond to the problem or problems each patient is facing with their chronic illness by evaluating both objective and subjective data from the patient about each of the conditions. With the subjective data, the present invention can also develop treatment plans that not only focus on treating the condition, but on treating the condition in a manner that minimizes the disruption on and quality of a patient's daily life.

The present invention also develops ongoing treatment plans that more effectively respond to the problem or problems each patient is facing with their chronic illness by using customized guidelines or algorithms which are based on each patient's particular medical history. With these customized guidelines, the present invention can also develop treatment plans that not only focus on more effectively treating the condition, but also on treating the condition in a manner that minimizes the disruption on and quality of a patient's daily life.

Additionally, the present invention provides notification directly to an emergency service provider when an emergency condition is detected. As a result, there is a higher chance that an emergency or potential emergency will be identified and treated as soon as possible.

Further, the present invention monitors physician and patient compliance with prescribed treatment guidelines, such as those provided by NIH. This monitoring should help provide physicians, medical facilities and organizations, such as HMO's and physician review boards, with important feedback on physician's compliance with treatment guidelines and the patient's compliance with treatment regimens.

BRIEF DESCRIPTION OF THE DRAWINGS

FIG. 7 is a screen shot of a home page of an interactive user interface on display on a display device in accordance with one embodiment of the present invention;

FIG. 8 is a screen shot of a first page of an interactive user interface on display on a display device used in accordance with one embodiment of the present invention;

FIGS. 9A and 9B are screen shots of a second page of an interactive user interface on a display on a display device used in accordance with one embodiment of the present invention;

FIGS. 10A and 10B are screen shots of a third page of an interactive user interface on a display on a display device used in accordance with one embodiment of the present invention;

FIG. 11 is a screen sheet of a page of an interactive user interface on display on a display device at the end of data collection used in accordance with one embodiment of the present invention; and FIGS. 12A–12C are screen shots of a page of an interactive user interface on a display on a display device used to review and confirm data entered in accordance with one embodiment of the present invention.

DETAILED DESCRIPTION

A system 10 and method for monitoring and treating a patient who has one or more diagnosed conditions or illnesses and is located at a remote location from a treatment processing system in accordance with one embodiment of the present invention is illustrated in FIGS. 1–6. Among other features, the present invention develops ongoing treatment plans that more effectively respond to the problem or problems each patient is facing with their chronic illness, as well as providing notification to emergency service providers in the event of an emergency and tracking physician compliance with prescribed treatment guidelines.

Figure 1:
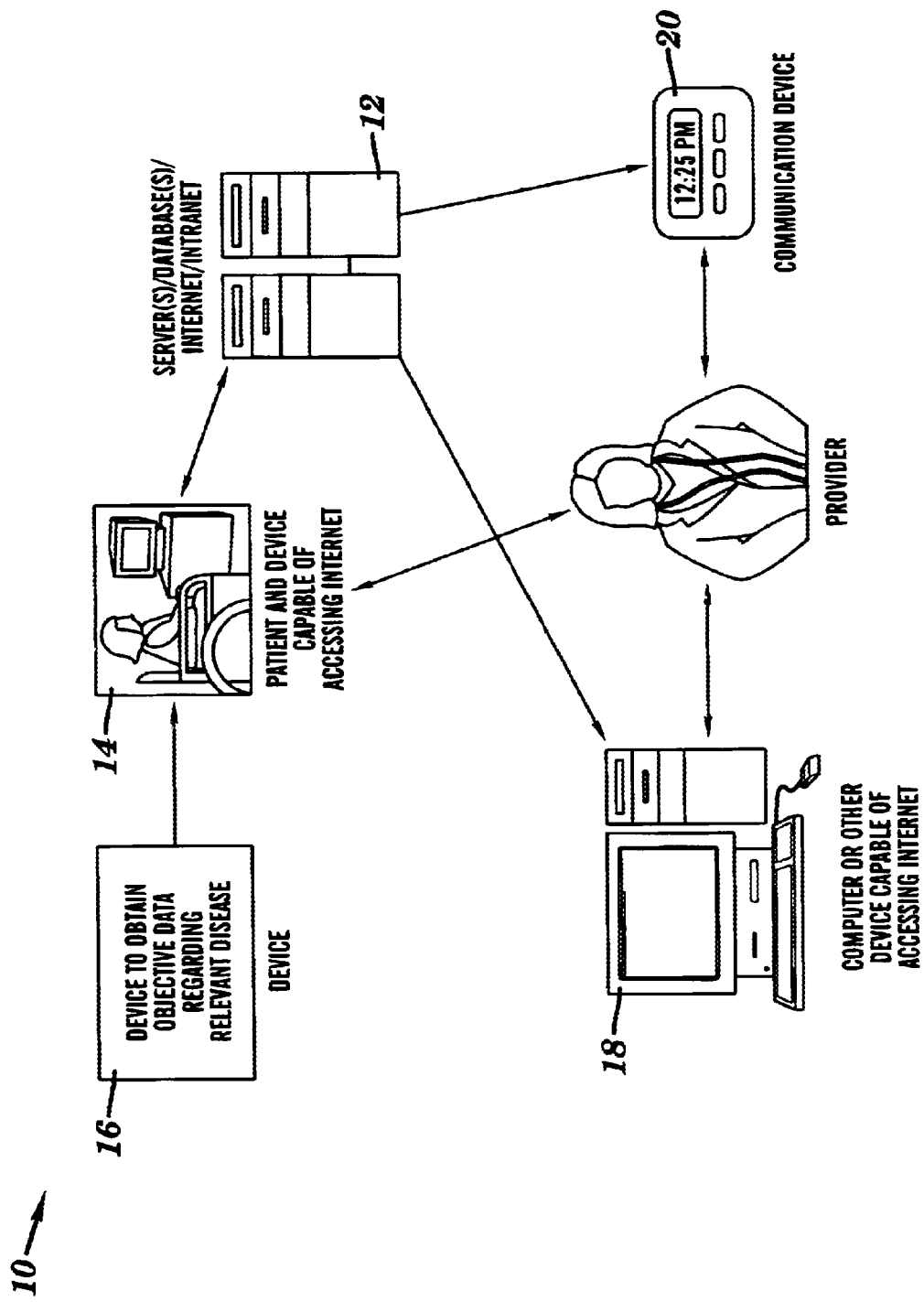
FIG. 1 is a block diagram of a system for monitoring and treating a patient who has one or more diagnosed conditions in accordance with one embodiment of the present invention.

Referring to FIG. 1, the system 10 includes a treatment processing system 12, a patient processing system 14, an optional self-monitoring device, an optional provider processing system 18, and an optional communication device 20 in this particular embodiment, although system 10 may have other components, other numbers of the components, and other combinations of the components. The patient processing system 14 is operatively coupled to the treatment processing system 12 which is operatively coupled to the provider processing system 18 and the communication device 20. A variety of communication systems and/or methods can be used to operatively couple and communicate between the treatment processing system 12 and the patient processing system 14, the provider processing system 18, and the communication device 20, including a direct connection, a local area network, a wide area network, the world wide web, modems and phone lines, or wireless communication technology each having communications protocols. Although one configuration for the system 10 is shown, other configurations are possible and envisioned.

The treatment processing system 12 includes at least one processor, at least one memory storage device, and at least one input/output user interface which are coupled together by a bus system or other link, although the treatment processing system 12 may comprise other components, other numbers of the components, and other combinations of the components. The processor executes a program of stored instructions for at least a portion of the method for monitoring and treating a patient who has one or more diagnosed conditions in accordance with one embodiment of the present invention as described herein and set forth in FIGS. 2–6. A variety of different types of memory storage devices, such as a random access memory (RAM) or a read only memory (ROM) in the system or a floppy disk, hard disk, CD ROM, or other computer readable medium which is read from and/or written to by a magnetic, optical, or other reading and/or writing system that is coupled to the processor, can be used to store the programmed instructions described herein as well as other information. The input/output user interface is used to operatively couple and communicate between the treatment processing system 12 and the patient processing system 14, the provider processing system 18, and the communication device 20. Although in his particular embodiment, the method in accordance with one embodiment of the invention is stored as programmed instructions in the treatment processing system 12 for execution by the treatment processing system 12, some or all of the programmed instructions could be stored and executed elsewhere. By way of example only, the programmable instructions could be stored and executed by the provider processing system 18 in communication with the patient processing system 14 without a separate treatment processing system 12.

The patient processing system 14 includes at least one processor, at least one memory storage device, at least one input/output user interface, at least one display device, and at least one user input device which are coupled together by a bus system or other link, although the patient processing system 14 may comprise other components, other numbers of the components, and other combinations of the components. The processor for the patient processing system 14 executes a program of stored instructions for at least a portion of the method for monitoring and treating a patient who has one or more diagnosed conditions in accordance with one embodiment of the present invention as described herein and set forth in FIGS. 2–6. A variety of different types of memory storage devices, such as a random access memory (RAM) or a read only memory (ROM) in the system or a floppy disk, hard disk, CD ROM, or other computer readable medium which is read from and/or written to by a magnetic, optical, or other reading and/or writing system that is coupled to the processor, can be used to store the programmed instructions described herein as well as other information. The input/output user interface is used to operatively couple and communicate between the patient processing system 14 and the treatment processing system 12 and may be used to operatively couple and communicate between the patient processing system 14 and the self monitoring device. The display device displays information for the operator, such as the updated treatment plan for the patient or a request to enter in objective and/or subjective data about one or more diagnosed conditions. A variety of different types of display devices can be used, such as a monitor, printer, or any other type of device which can convey information to the user of the patient processing system 14. The user input device enables an operator to generate and transmit signals or commands to the patient processing system 14. A variety of different types of user input devices can be used, such as a keyboard, computer mouse, or any other user input device which provides a mechanism for a user or operator.

In this particular embodiment, one self monitoring device is illustrated, although the number of self monitoring devices can vary as needed for the particular patient or disease. The self monitoring device is used by the patient or other individual assisting the patent to gather objective data about one or more of the patient's diagnosed conditions. The self monitoring device may be operatively coupled to the patient processing system 14 to transfer the objective data gathered by the device or the objective data can be entered in manually by the patient or other operator. A variety of different types of self-monitoring devices can be used, such as a peak flow measuring device, a blood sugar measurement device, or a blood pressure measuring device.

The provider processing system 18 includes at least one processor, at least one memory storage device, at least one input/output user interface, at least one display device, and at least one user input device which are coupled together by a bus system or other link, although the provider processing system 18 may comprise other components, other numbers of the components, and other combinations of the components. The processor for the provider processing system 18 executes a program of stored instructions for at least a portion of the method for monitoring and treating a patient who has one or more diagnosed conditions in accordance with one embodiment of the present invention as described herein and set forth in FIGS. 2–6. A variety of different types of memory storage devices, such as a random access memory (RAM) or a read only memory (ROM) in the system or a floppy disk, hard disk, CD ROM, or other computer readable medium which is read from and/or written to by a magnetic, optical, or other reading and/or writing system that is coupled to the processor, can be used to store the programmed instructions described herein as well as other information. The input/output user interface is used to operatively couple and communicate between the provider processing system 18 and the treatment processing system 12 and may be used to operatively couple and communicate between the provider processing system 18 and the self monitoring device. The display device displays information for the operator, such as the updated treatment plan for the patient or a request to enter in objective and/or subjective data about one or more diagnosed conditions. A variety of different types of display devices can be used, such as a monitor, printer, or any other type of device which can convey information to the user of the provider processing system 18. The user input device enables an operator to generate and transmit signals or commands to the provider processing system 18. A variety of different types of user input devices can be used, such as a keyboard, computer mouse, or any other user input device which provides a mechanism for a user or operator.

In this particular embodiment, one communication device 20 is illustrated, although the number of communication devices can vary as needed for the particular patient. The communication device 20 is used by the patient or other individual assisting the patent to gather objective data about one or more of the patient's diagnosed conditions. The communication device 20 may be operatively coupled to communicate with the treatment processing system 12 to, for example, receive information about the assessment and/or proposed modifications to a patient's treatment plan or to notify an emergency service provider of an emergency. A variety of different types of communication devices can be used, such as a pager or a wireless telephone.

The operation of system 10 and method for monitoring and treating a patient who has one or more diagnosed conditions and is located at a remote location from a treatment processing system 12 in accordance with one embodiment of the present invention will be discussed with reference to FIGS. 1–12C.

Figure 2:
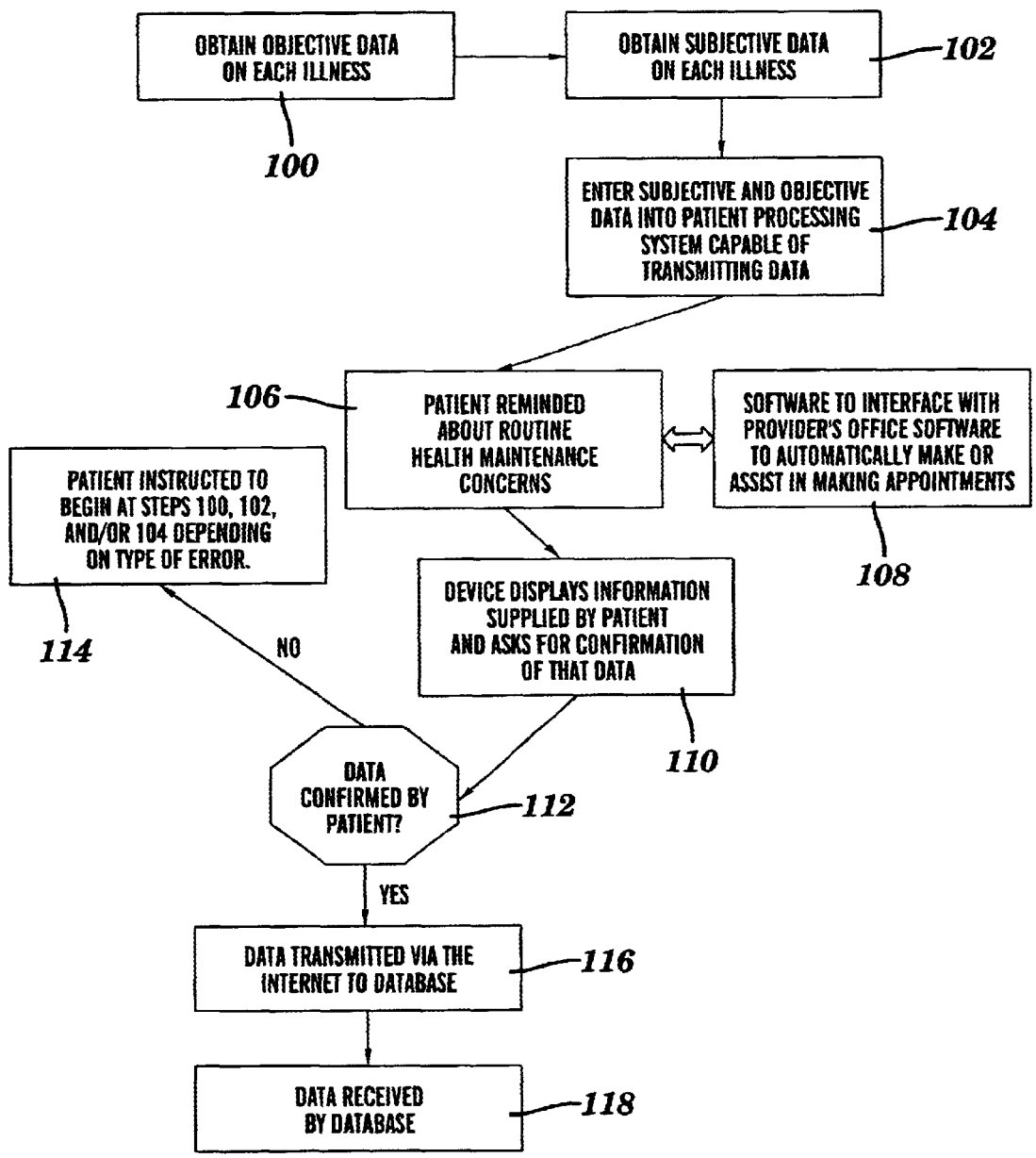
FIG. 2 is a flow chart of a method for obtaining data from a patient who has one or more diagnosed conditions in accordance with one embodiment of the present invention.

Referring to FIG. 2, at step 100 the method in accordance with one embodiment of the present invention begins and the patient or other individual assisting the patient uses the self-monitoring device to obtain objective data for the relevant illness or illnesses. A variety of different types of self-monitoring devices may be used depending upon the type of objective data that is sought. By way of example only, if the patient were diabetic they would obtain a finger stick blood glucose level.

Next, in this particular embodiment at step 102 the patient makes a subjective self-evaluation of each of the diagnosed conditions to obtain subjective data. The subjective data can include a variety of different types of subjective information, including symptomatology and the patient's subjective feelings on his or her well being. Typically, the subjective data will be obtained in response to specific inquiries received by the patient through the patient processing system 14 and displayed on the display device coupled to the patient processing system 14, although the subjective data can be obtained in other manners. By way of example only, if the patient were diabetic they would subjectively gauge their wellness and severity of symptoms. Additionally, in this particular embodiment, the patient also enters data or information on the patient's actual implementation of the treatment plan, such as the patient's usage of pharmaceuticals and other medical devices. The type of and amount of data or information and entered here can vary based on the particular application.

Next at step 104, the patient enters or facilitates the entry of the objective and/or the subjective data to the patient processing system 14 using the user input device, such as a keyboard or mouse. As discussed earlier, the self monitoring devices may be operatively coupled to the patient processing system 14 and/or to the treatment processing system 12 to automatically transfer the objective data obtain about the patient's condition. By way of example only, some screen shots of user interfaces for collecting objective and subjective data from the patient are illustrated in FIGS. 7, 8, 9A, 9B, 10A, 10B, and 11. The types of and number of questions asked and data collected can vary as need for the particular application. The exemplary screen shots in this particular embodiment are related to an application for monitoring and treating a patient with asthma, although the screen shots can be modified to solicit data on a variety of different types of conditions, such as diabetes or a heart condition. The patient would see these user interfaces on the display of the patient processing system 14 and would respond to questions on the user interface using a user input device, such as a keyboard or mouse, for the patient processing system 14.

Referring back to FIG. 2, at step 106, the patient may also receive reminders generated by the patient processing system 14 or from a transmission from the treatment processing system 12 regarding other health care related matters, such as reminders for immunization and in person check-ups. In step 108, the patient at the patient processing system 14 can interface with the provider at the provider processing center regarding the other health care related matters, such as assisting the patient in making appointments for immunizations or in-person check-ups.

Next in step 110, the display device at the patient processing system 14 displays the objective and/or subjective data supplied by the patient and requests confirmation of the each piece of data by the patient. By way of example only, some screen shots of user interfaces for reviewing and confirming the objective and subjective data from the patient are illustrated in FIGS. 12A–12C. The process for reviewing and confirming entered data as well as the type data reviewed can vary as need for the particular application. Referring back to FIG. 2, in this particular embodiment using the user input device, such as a mouse or keyboard, in step 112 the patient enters a response to the request to confirm each piece of the data into the patient processing system 14 which is transmitted to the treatment processing system 12. Although in this particular example, a confirmation for all of the objective and subjective data is sought, other variations for confirming the data may be sought, such as a confirmation of just a portion of the data.

If the data is not confirmed by the patient, then the No branch is taken from step 112 to step 114. In step 114, the patient is referred back to step 100 or 102 depending upon which portion of the data was not confirmed and then the steps subsequent to that step would be repeated again as described above. If the data is confirmed by the patient, then the Yes branch is taken from step 112 to step 116.

In step 116, the confirmed objective data and subjective data is transmitted from the patient processing system 14 to the treatment processing system 12. Next, in step 118 the confirmed objective data and subjective data is received by the treatment processing system 12, although the data could be received by other processing systems, such as the provider processing system 18.

Figure 3:
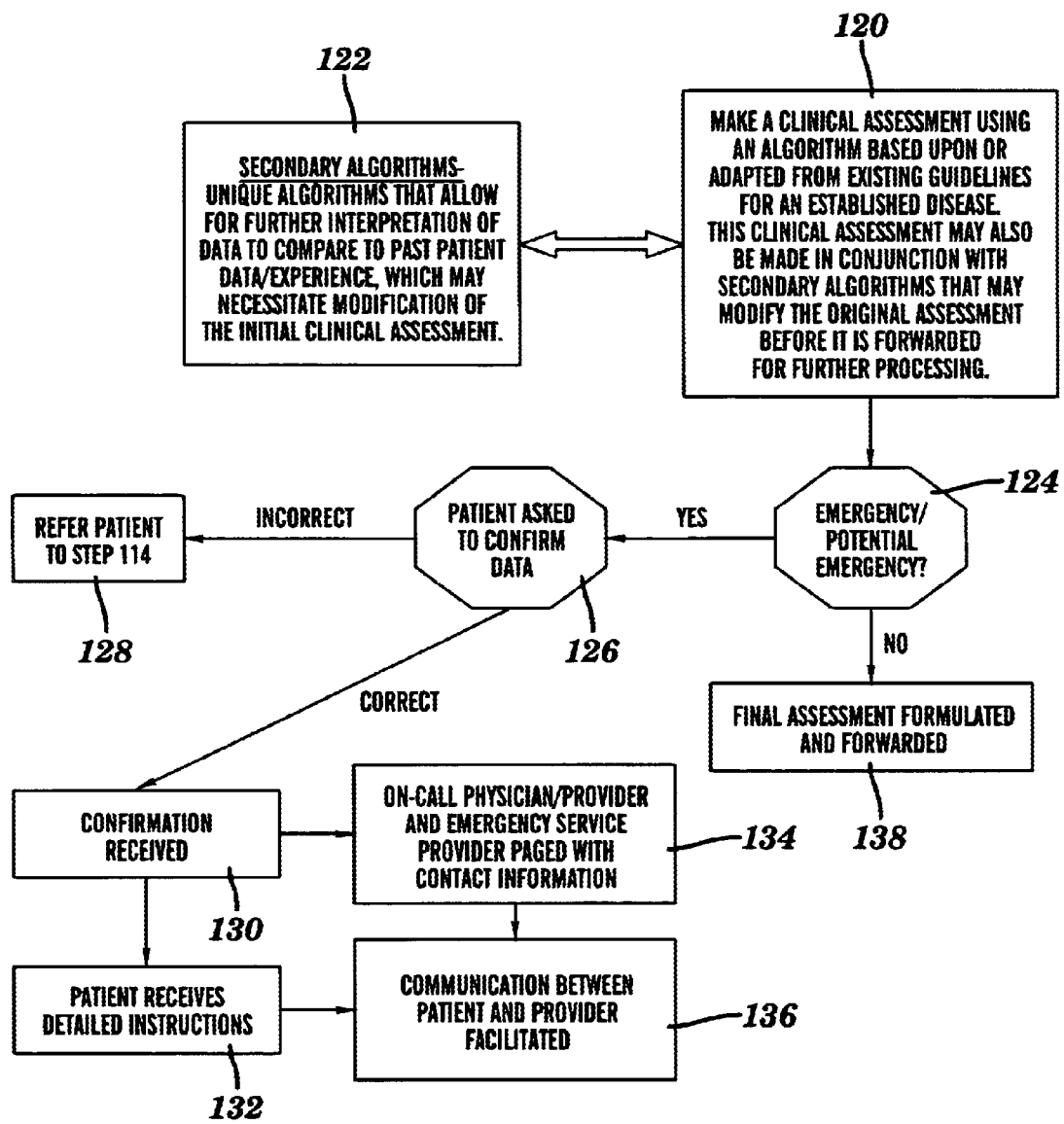
FIG. 3 is a flow chart of a method for assessing each of the diagnosed conditions of the patient in accordance with one embodiment of the present invention.

Referring to FIG. 3, in step 120 a clinical assessment of each of the patient's diagnosed conditions is made using an algorithm for each of the diagnosed conditions which is stored as programmable instructions in the treatment processing system 12 in this particular embodiment. Each of the algorithms represents or is adapted from established guidelines for clinical assessment of an established disease, such as asthma or diabetes, from a source, such as the NIH or another authoritative organization.

The clinical assessment being made in step 120 may also be made in conjunction with secondary algorithm or algorithms in step 122. The secondary algorithm or algorithms provide further interpretation of the newly received objective data and/or the subjective data from the patient and may necessitate modification of the initial clinical assessment. A variety of different types of secondary algorithms tailored to each patient based on the patient prior history can be used. In this particular embodiment, the secondary algorithms are based on past objective and subjective data on the diagnosed conditions from the patient and also prior experience with the patient relating to these diagnosed conditions and prior treatment plans. By way of example only, a secondary algorithm might utilize information on a patients' risk factors, comorbidities, age, gender, past response to therapeutic intervention, and other objective/subjective data not initially received from the patient to make and/or adjust the clinical assessment.

Figure 6:
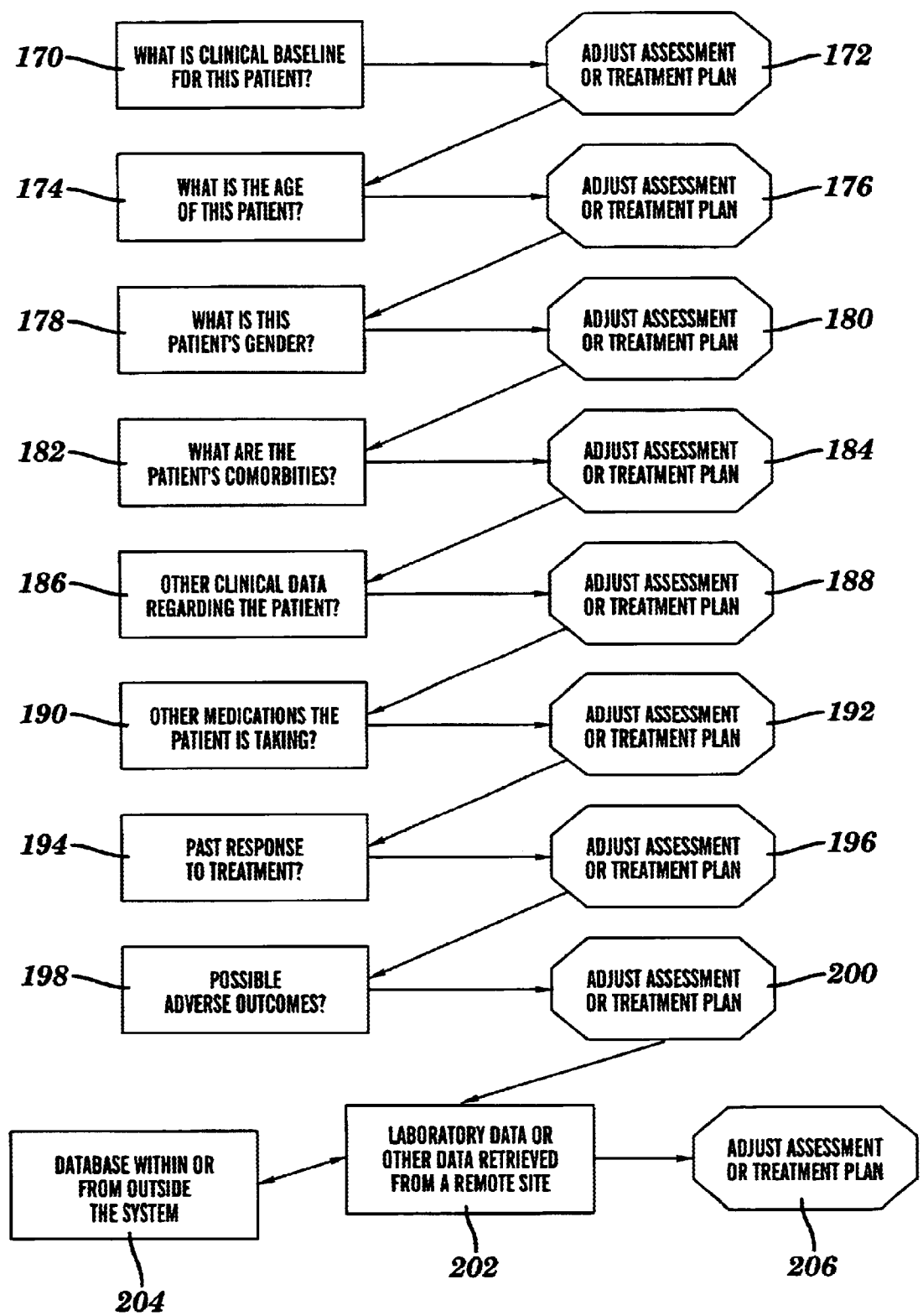
FIG. 6 is a flow chart of a method for modifying an assessment and/or a treatment plan based on prior information about that particular patient in accordance with one embodiment of the present invention.

Referring to FIG. 6, one example of a secondary algorithm used to possibly adjust the assessment in this particular embodiment is illustrated. In this example, in step 170 a clinical baseline for the patient is obtained from a memory device or by inquiring from another source, such as a provider processing system 18. Next, in step 172 the assessment being determined in step 120 may be adjusted based on the information obtained in step 170. Next, in step 174 the patient's age is obtained from a memory device or by inquiring from another source, such as the patient processing system 14. Next, in step 176 the assessment being determined in step 120 may be adjusted based on the information obtained in step 174. Next, in step 178 the patient's gender is obtained from a memory device or by inquiring from another source, such as the patient processing system 14. Next, in step 180 the assessment being determined in step 120 may be adjusted based on the information obtained in step 178. Next, in step 182 the patient's comorbities are obtained from a memory device or by inquiring from another source, such as the patient processing system 14. Next, in step 184 the assessment being determined in step 120 may be adjusted based on the information obtained in step 182. Next, in step 186 other clinical data about the patient is obtained from a memory device or by inquiring from another source, such as the patient processing system 14 or the provider processing system 18. Next, in step 188 the assessment being determined in step 120 may be adjusted based on the information obtained in step 186. Next, in step 190 other medication(s) the patient is taking are obtained from a memory device or by inquiring from another source, such as the patient processing system 14 or provider processing system 18. Next, in step 192 the assessment being determined in step 120 may be adjusted based on the information obtained in step 190. Next, in step 194 the patient's past response to treatment ss obtained from a memory device or by inquiring from another source, such as the patient processing system 14 or provider processing system 18. Next, in step 196 the assessment being determined in step 120 may be adjusted based on the information obtained in step 194. Next, in step 198 possible adverse outcomes in the patient's history are obtained from a memory device or by inquiring from another source, such as the patient processing system 14 or provider processing system 18. Next, in step 200 the assessment being determined in step 120 may be adjusted based on the information obtained in step 198. Next, in steps 202 and 204 laboratory data and/or other data for the patient's age is obtained from a memory device within or outside the system. Next, in step 206 the assessment being determined in step 120 may be adjusted based on the information obtained in steps 202 and 204. Although one example of a secondary algorithm is shown, a variety of different types of algorithms or processes based on a patient's prior data or history could be used. One or more of the pieces of information obtained in steps 170, 174, 178, 182, 186, 190, 194, 198, 202, and 204, could be considered and analyzed together to adjust the assessment being determined in step 120. Additionally, a variety of other pieces of information about the patient which are not shown could also be obtained and used to adjust the assessment depending upon the particular application. For example, a secondary algorithm used to adjust an assessment being made for a patient with asthma would be different from one for a patient with diabetes. The secondary algorithm for assessing and/or treating asthma might use information about a patient's prior peak flow readings with prior treatment plans while a secondary algorithm for assessing and/or treating diabetes might use information about a patients prior blood sugar levels with prior treatments.

Referring back to FIG. 3, in step 124, a determination is made whether any of the clinical assessments for the patient indicate a potential emergency or an actual emergency by the treatment processing system 12, although other processing systems in system 10 could be used. This determination is made using an algorithm with established guidelines or criteria for determining if an potential emergency or actual emergency exists. By way of example only, if the objective data relates to the patient's blood pressure and heart rate and this objective data is above or below certain set or established thresholds then a potential emergency or actual emergency will be declared by the treatment processing system 12.

If no potential emergency or actual emergency is determined in step 124, then the No branch is taken to step 138. In step 138, the final clinical assessment or assessments for each of the diagnosed conditions is formulated by the treatment processing system 12, although other processing systems in system 10 could be used. Additionally, in this particular embodiment in step 138 if sub-optimal clinical performance is detected, but it is not detected to be an emergency or potential emergency a notice to the patient's physician is sent via appropriate modalities of the non-emergent, but sub-optimal performance, such as to the communication device 120 and/or to provide processing system 18.

If a potential emergency or actual emergency is determined in step 124, then the Yes branch is taken to step 126. In step 126, a request is sent to the patient processing system 14 for the patient to confirm some or all of the objective and/or subjective data or otherwise state whether some or all of the objective and/or subjective data is correct, although the request could be sent to the patient in other manners and using other devices, such as another communication device 20. If the patient responds that some or all of the objective and/or subjective data is incorrect using user input device to the patient processing system 14, then the Incorrect or No branch is taken to step 128. In step 128, the patient is referred back to step 114 to correct the error or errors in the objective and/or subjective data entered. Although in this particular embodiment the confirmation is sent using the patient processing system 14, other manners and using other devices, such as another communication device 20.

If the patient responds that some or all of the objective and/or subjective data is correct, then the Correct or Yes branch is taken to step 130 where the treatment processing system 12 receives the confirmation from the patient that the data is correct.

Next in step 132, the treatment processing system 12 sends detailed instructions to the patient processing system 14 for the patient to view of the display and implement relating to how to respond to the potential or actual emergency, e.g. instruction to call an ambulance or to take a certain amount of a medication, although other manners and/or devices for communicating these instructions to the patient could be used. Meanwhile in step 134, the provider or physician treating the patient or another provider, such as an ambulance service or other emergency server is contacted about the existence of and information about the detected potential or actual emergency with the patient, including patient contact information. As a result, in the event of a potential emergency or an actual emergency, emergency care can be dispatched to the patient as soon as possible. Next in step 136, communication between the patient at the patient processing system 14 and the provider at the provider processing system 18 is facilitated. In this particular embodiment, the communication is facilitated through the internet using e-mail, although other manners and/or devices for communicating these instructions to the patient could be used.

Figure 4:
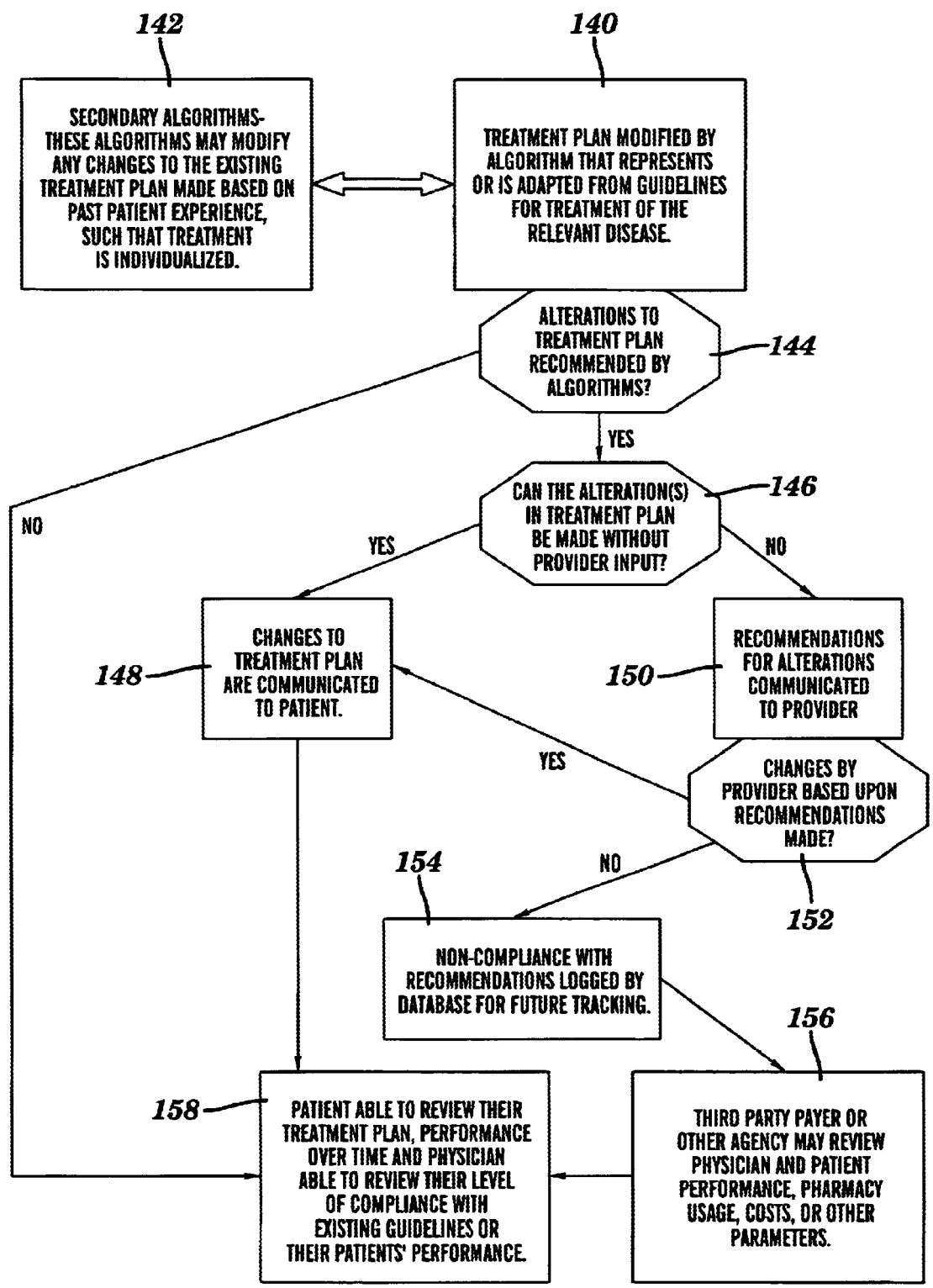
FIG. 4 is a flow chart of a method for updating a treatment plan for each of the diagnosed conditions of the patient in accordance with one embodiment of the present invention.

Referring to FIG. 4, in step 140 an existing treatment plan for each of the diagnosed conditions is retrieved from a memory storage device in the treatment processing system 12 and is then updated or modified by the treatment processing system 12 based on the clinical assessment from step 138. Although the treatment plans could be stored elsewhere and the treatment plan can be updated or modified by other processing systems in system 10. More specifically, the treatment plan is updated or modified using the clinical assessment from step 138 and an algorithm that represents or is adapted from established guidelines for treatment of relevant the disease or illness, such as the guidelines from NIH. Based on the clinical assessment, the algorithm may determine that no modification or update to the existing treatment plan is necessary and in that case the updated treatment plan will be the existing treatment plan. In step 140, in determining the updated treatment plan, the system 10 may compare the updated treatment plan with the prior treatment plan and/or the treatment plan being carried out by the patient, i.e. the patient may not be following some or all of the prior instructions in the treatment plan. For example, if a patient is not following an existing treatment plan and is missing doses of his/her medication, then the update treatment plan may not change the dosage of the medication, but instead will simply inform the patient to follow the originally prescribed treatment plan.

The treatment plan being updated or modified in step 140 may also be modified or updated in conjunction with a secondary algorithm or algorithms in step 142 in the treatment processing system 12, although other processing systems in system 10 could be used. The secondary algorithm or algorithms provide further interpretation of the updated treatment plan and may necessitate or eventuate modification of the updated treatment plan in step 140. A variety of different types of secondary algorithms tailored to each patient based on the patient prior history can be used. In this particular embodiment, the secondary algorithms are based on prior experience with the patient relating to the prior treatment plans. By way of example only, one example of a secondary algorithm used to possibly adjust the treatment plan in this particular embodiment is illustrated in FIG. 6. Since this flowchart has been described earlier, the process will not be described again here except that in steps 172, 176, 180, 184, 188, 192, 196, 200, and/or 206 an adjustment to the treatment plan being determined in step 140 may be made based on one or more piece of information or data obtained in steps 170, 174, 178, 182, 186, 190, 194, 198, 202, and 204 in this example. Additionally, a variety of other pieces of information about the patient's prior history or other data or information which are not shown could also be obtained and used to adjust the treatment plan depending upon the particular application.

In step 144, a determination is made on whether a modification or modifications to the existing treatment plan for each diagnosed condition has been made in step 140 and/or step 142. If no modifications were made to the existing treatment plan for each diagnosed condition, then the update treatment plan is the existing treatment plan and the No branch is taken from step 144 to step 158. In step 158, the updated treatment plans are displayed on the display device by the patient processing system 14 for review and application by the patient, although other methods and devices for communicating the updated treatment plan or plans to the patient could be used.

If a modification or modifications was/were made to the existing treatment plan for at least one of the diagnosed conditions, then the Yes branch is taken from step 144 to step 146 for each updated treatment plan with at least one modification. In step 146, a determination is made on whether the modification or modifications to the existing treatment plan can be made without approval from a provider. In this particular embodiment, the treatment processing system 12 makes this determination, although other processing systems in system 10 could be used to make this determination. By way of example only, a modification to prescribe a new medication for the diagnosed condition would require input from the provider.

If approval is not required for the modification or modifications to the existing treatment plan for one of the diagnosed conditions and it is logistically possible to make the modification or modifications, then the Yes branch is taken from step 146 to step 148 for that updated treatment plan. In step 148, the updated treatment plan with the modification or modifications is communicated from the treatment processing system 12 to the patient processing system 14. In step 158, the updated treatment plans are displayed on the display device for the patient processing system 14 for review and application by the patient, although other methods and devices for communicating the updated treatment plan or plans to the patient could be used.

If approval is required for the modification or modifications to the existing treatment plan for one of the diagnosed conditions, then the No branch is taken from step 146 to step 150. In step 150, the modification or modifications to the existing treatment plan are transmitted from the treatment processing system 12 to the provider processing system 18, although other manners and/or device for communicating the modification or modifications to the existing treatment plan can be used. In this particular embodiment, the modification or modifications to the existing treatment plan are displayed by the display device for the provider processing system 18 for review by the provider. The provider using the user input device for the provider processing system 18 can accept the modification or modifications to the existing treatment plan or can make one or more modifications to the updated treatment plan. The acceptance of or the modification or modifications to the updated treatment plan are transmitted back to the treatment processing system 12 in this particular embodiment. By way of example only, the provider may review a recommendation to prescribe a new medication for the patient to treat one of the diagnosed conditions and either accept the recommendation or change the prescription to a different medication.

Next, in step 152 a determination is made by the treatment processing system 12 on whether the modification or modifications to the updated treatment plan are in compliance with the recommended modification or modifications the modification or modifications to the existing treatment plan made earlier in steps 140 and 142, although other processing system could be used. If the modification or modifications to the updated treatment plan are in compliance with the modification or modifications to the existing treatment plan made earlier then the Yes branch is taken from step 152 to step 148 (described earlier). In step 152, the patient may simply be notified to be more compliant with the prescribed treatment plan.

If the modification or modifications to the updated treatment plan are in not compliance with the modification or modifications to the existing treatment plan made earlier then the No branch is taken from step 152 to step 154. In step 154, the providers noncompliance with the modification or modifications to the existing treatment plan recommended by the system 10 is recorded and stored in a memory storage device in the treatment processing system 12, although the information on non-compliance could be stored elsewhere. In optional step 156, another processing system, such as a medical facility, insurance company, or review board, may be operatively coupled to the system 10 and may access the stored information on non-compliance to evaluate the performance of different health care providers. In step 156, each patient's compliance with treatment plans can be monitored and analyzed. By way of example, non-compliant patients may be notified of their non-compliance and a physician's modifications to treatment plans may take into account patient compliance to treatment protocols.

Next, in step 158 as discussed earlier the updated treatment plans are displayed on the display device for the patient processing system 14 for review and application by the patient. Additionally, in step 158, a provider's performance over time with respect to complying with established guidelines for assessing conditions in patients and for treating conditions can be analyzed for a variety of reasons. By way of example only, a third party payer could review both patient and physician performance in the system 10, such as their clinical performance over time, compliance with established treatment guidelines/recommendations for one and for multiple patients, overall cost, pharmacy usage and overall wellness. For example, a patient finishes session and can review their clinical performance over time via graphic displays and then returns to Step 100 at the appropriate time. Additionally, another authorized agency, such as a pharmaceutical company or university could review data stored for purposes of research, post-marketing analysis, appraisal of the efficacy of a particular product or device, comparison of two or more similar treatments or devices, or to conduct clinical or field trials of new or existing devices or pharmaceuticals or other such activities consistent with their charter. Further, as discussed earlier, patient compliance with treatment plans can also be analyzed in step 158.

Figure 5:
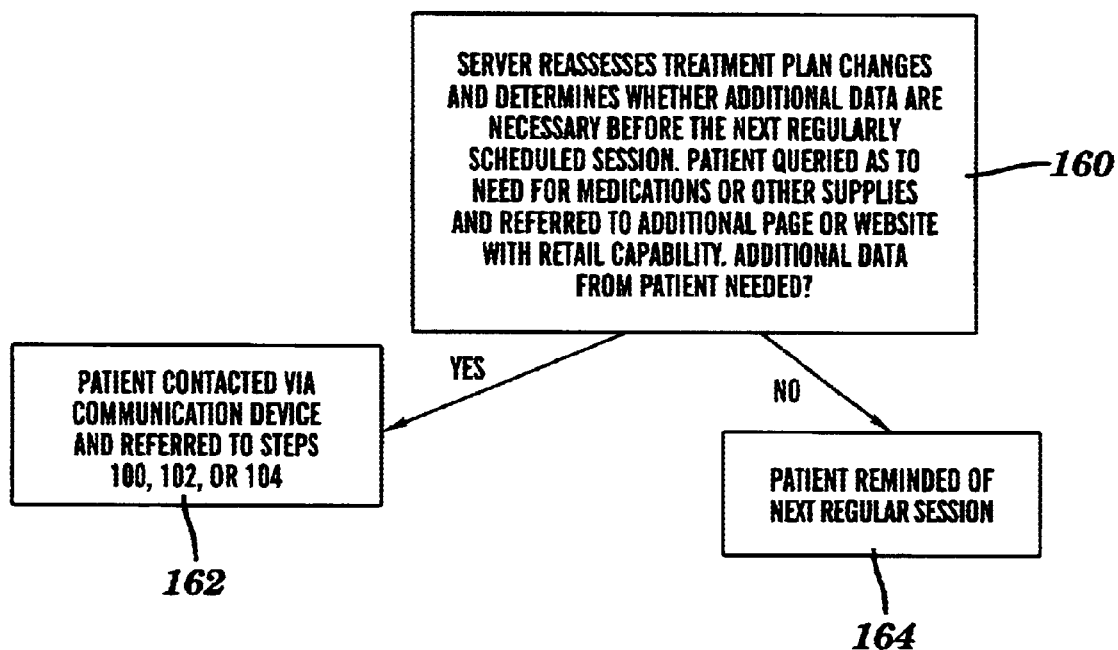
FIG. 5 is a flow chart of a method for obtaining more information relating to the updated treatment plan in accordance with one embodiment of the present invention.

Referring to FIG. 5, in step 160 the treatment processing system 12 reassesses the modification or modifications to the updated treatment plan or plans and determines whether additional objective and/or subjective data is needed from the patient prior to the next regularly scheduled session. Additionally, the treatment processing system 12 queries the patient processing system 14 to determine if the patient needs other items, such as refills on medications or other medical supplies, although other manners and devices for requesting this information can be used. If other items are needed, then the treatment processing system 12 may arrange for them to be delivered to the patient. If more information is needed, then the Yes branch is taken from step 160 to step 162. In step 162, the treatment processing system 12 contacts the patient through the patient processing system 14 and request this additional objective and/or subjective data asset forth in steps 100 and 102, although other manners and devices for requesting this objective and/or subjective data can be used. If more objective and/or subjective data is not needed, then the No branch is taken from step 160 to step 164 and the treatment processing system 12 transmits a reminder to the patient processing system 14 of the date of the next session, although other manners and devices for transmitting this information can be used.

The present invention as discussed herein can be implemented on a single program general purpose computer or separate program general purpose computer. The present invention can also be implemented on a special purpose computer, a programmed microprocessor or microcontroller and peripheral integrated circuit element, an ASIC or other integrated circuit, a digital signal processor, a hard wired electronic or logic circuit such as a discrete element circuit, a programmable logic device such as a PLD, PLA, FPGA, PAL, or the like. In general, any device capable of implementing a finite state machine that is in turn capable of implementing the flowchart illustrated in FIGS. 2–6 can be used to implement the system 10 according to this invention.

Furthermore, the disclosed method may be readily implemented in software using object or object-oriented software development environments that provide portable source code that can be used on a variety of computer or workstation hardware platforms. Alternatively, the disclosed system may be implemented partially or fully in hardware using standard logic circuits or VLSI design. Whether software or hardware is used to implement the system in accordance with this invention is dependent on the speed and/or efficiency requirements of the system, the particular function, and the particular software or hardware systems or microprocessor or microcomputer systems being utilized. The system and methods described above, however, can be readily implemented in hardware and/or software using any known or later-developed systems or structures, devices and/or software by those skilled in the applicable art without undue experimentation from the functional description provided herein together with a general knowledge of the computer arts.

Moreover, the disclosed methods may be readily implemented as software executed on a programmed general purpose computer, a special purpose computer, a microprocessor, or the like. In this instance, the methods and systems of this invention can be implemented as a routine embedded on a personal computer, such as a Java®, CGI script or other programming languages, techniques, and/or strategies, as a resource residing on a server or graphics workstation, as a routine embedded in a dedicated computer controlled display system, a web browser, an computer controlled display for a cellular phone, a PDA, a dedicated computer controlled display system, or the like. The system can also be implemented by physically incorporating the system and method into a software and/or hardware system, such as the hardware and software systems of a dedicated computer system.

Having thus described the basic concept of the invention, it will be rather apparent to those skilled in the art that the foregoing detailed disclosure is intended to be presented by way of example only, and is not limiting. Various alterations, improvements, and modifications will occur and are intended to those skilled in the art, though not expressly stated herein. These alterations, improvements, and modifications are intended to be suggested hereby, and are within the spirit and scope of the invention. Accordingly, the invention is limited only by the following claims and equivalents thereto.

What is claimed is:

1. A method for tracking compliance with treatment guidelines, the method comprising:

determining a current assessment of one or more diagnosed conditions in a patient based on data about each of the diagnosed conditions from the patient who is at a remote location and on one or more assessment guidelines for each of the diagnosed conditions;

updating an existing treatment plan for each of the diagnosed conditions based on the existing treatment plan, the current assessment, and on one or more treatment guidelines for each of the diagnosed conditions to generate an updated treatment plan for each of the diagnosed conditions;

reviewing the updated treatment plan for each of the diagnosed conditions;

determining if one or more changes are needed to the reviewed treatment plan for each of the diagnosed conditions;

changing the reviewed treatment plan if the one or more changes are determined to be needed;

providing the patient with the reviewed treatment plan for each of the diagnosed conditions; and generating and providing compliance data based on the updated treatment plan and the reviewed treatment plan for each of the diagnosed conditions.

2. The method as set forth in claim 1 wherein the compliance data comprises provider information on the number of the reviewed treatment plans which are different from a corresponding one of the updated treatment plans for each provider.

3. The method as set forth in claim 1 wherein the compliance data further comprises data on patient compliance with at least one of the existing treatment plan for each diagnosed condition.

4. A system for tracking compliance in treating patients, each of the patients having one or more diagnosed conditions, the system comprising:

an assessment processing system that determines a current assessment of each of the diagnosed conditions based on data about each of the diagnosed conditions from the patient who is at a remote location and on one or more assessment guidelines for each of the diagnosed conditions;

a treatment processing system that updates an existing treatment plan for each of the diagnosed conditions based on the existing treatment plan, the current assessment, and on one or more treatment guidelines for each of the diagnosed conditions to generate an updated treatment plan for each of the diagnosed conditions;

a review system that modifies the updated treatment plan if one or more changes are determined to be needed and provides a reviewed treatment plan;

a presentation system that provides the reviewed treatment plan for each of the diagnosed conditions; and a compliance system that generates and provides compliance data based on the reviewed treatment plan and the updated treatment plans.

5. The system as set forth in claim 4 wherein the compliance data comprises provider information on the number of the reviewed treatment plans which are different from a corresponding one of the updated treatment plans for each provider.

6. The system as set forth in claim 4 wherein the compliance data further comprises data on patient compliance with at least one of the existing treatment plan for each diagnosed condition.

7. A computer readable medium having stored thereon instructions for tracking compliance with treatment guidelines which when executed by a processor, cause the processor to perform the steps of:

determining a current assessment of one or more diagnosed conditions in a patient based on data about each of the diagnosed conditions from the patient who is at a remote location and on one or more assessment guidelines for each of the diagnosed conditions;

updating an existing treatment plan for each of the diagnosed conditions based on the existing treatment plan, the current assessment, and on one or more treatment guidelines for each of the diagnosed conditions to generate an updated treatment plan for each of the diagnosed conditions;

reviewing the updated treatment plan for each of the diagnosed conditions;

determining if one or more changes are needed to the reviewed treatment plan for each of the diagnosed conditions;

changing the reviewed treatment plan if the one or more changes are determined to be needed;

providing the patient with the reviewed treatment for each of the diagnosed conditions; and generating and providing compliance data based on the updated treatment plan and the reviewed treatment plan for each of the diagnosed conditions.

8. The medium as set forth in claim 7 wherein the compliance data comprises provider information on the number of the reviewed treatment plans which are different from a corresponding one of the updated treatment plans for each provider.

9. The medium as set forth in claim 7 wherein the compliance data further comprises data on patient compliance with at least one of the existing treatment plan for each diagnosed condition.

* * * * *